United States Patent
Clark et al.

(10) Patent No.: US 9,302,253 B2
(45) Date of Patent: Apr. 5, 2016

(54) CATALYST AND PROCESS FOR THE PRODUCTION OF ACETIC ACID AND DIMETHYL ETHER

(71) Applicant: BP Chemicals Limited, Middlesex (GB)

(72) Inventors: Thomas Edward Clark, East Yorkshire (GB); David John Law, East Yorkshire (GB); Bruce Leo Williams, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 13 days.

(21) Appl. No.: 14/378,444

(22) PCT Filed: Feb. 22, 2013

(86) PCT No.: PCT/EP2013/053528
§ 371 (c)(1),
(2) Date: Aug. 13, 2014

(87) PCT Pub. No.: WO2013/124404
PCT Pub. Date: Aug. 29, 2013

(65) Prior Publication Data
US 2015/0352535 A1   Dec. 10, 2015

(30) Foreign Application Priority Data

Feb. 23, 2012  (EP) .................................... 12250049

(51) Int. Cl.
*B01J 29/65* (2006.01)
*C07C 67/37* (2006.01)
*C07C 41/09* (2006.01)
*C01B 39/44* (2006.01)
*C07C 51/09* (2006.01)

(52) U.S. Cl.
CPC ................. *B01J 29/65* (2013.01); *C01B 39/44* (2013.01); *C07C 41/09* (2013.01); *C07C 51/09* (2013.01); *C07C 67/37* (2013.01)

(58) Field of Classification Search
CPC ................................ C07C 51/09; C07C 41/16
See application file for complete search history.

(56) References Cited

U.S. PATENT DOCUMENTS

| 6,521,783 B1 | 2/2003 | Wegman et al. |
| 2009/0326281 A1 | 12/2009 | Appel et al. |

FOREIGN PATENT DOCUMENTS

| GB | EP2292578 A1 * | 3/2011 |
| KR | 2009131560 | 7/1995 |
| KR | 2009 0103512 A | 10/2009 |
| KR | 2009131560 | 12/2009 |
| WO | WO 95/18084 A1 | 7/1995 |
| WO | 2011/027105 A1 | 3/2011 |

OTHER PUBLICATIONS

Lewis et al, AIChE Journal, Permeation Studies on Oriented Single-Crystal Ferrierite Membranes, 1997, 43(1), pp. 83-90.*
Seung-Chan Baeu, et al; "Influence of catalytic functionalities of zeolites on product selectivities in methanol conversion"; *Energy & Fuels*, vol. 23(2), pp. 593-598 (2009).
Khandan, N., et al; "Determining an optimum catalyst for liquid phase dehydration of methanol to dimethyl ether"; *Applied Catalysis: General*, vol. 349, Issues 1-2, pp. 6-12 (2008).

* cited by examiner

*Primary Examiner* — Paul A Zucker
(74) *Attorney, Agent, or Firm* — Nixon & Vanderhye P.C.

(57) ABSTRACT

Process for the co-production of acetic acid and dimethyl ether products from a mixture of methanol and methyl acetate by contacting the mixture at a temperature from 200 to 260° C., with a catalyst composition containing a zeolite possessing a 2-dimensional channel system. The catalyst system contains at least one channel having a 10-membered ring and a silica:alumina molar ratio of at least 22:1.

19 Claims, No Drawings

CATALYST AND PROCESS FOR THE PRODUCTION OF ACETIC ACID AND DIMETHYL ETHER

This application is the U.S. national phase of International Application No. PCT/EP2013/053528 filed Feb. 22, 2013 which designated the U.S. and claims priority to European Patent Application No. 12250049.9 filed Feb. 23, 2012, the entire contents of each of which are hereby incorporated by reference.

The present invention relates to a process for the co-production of acetic acid and dimethyl ether from methanol and methyl acetate carried out at high temperature and in the presence of catalyst compositions comprising zeolites having high silica:alumina molar ratios.

It is known to catalyse the dehydration of methanol to dimethyl ether with zeolitic catalysts. The use of ferrierite in its hydrogen form to catalyse the dehydration of methanol is described, for example in the publications US 20090326281A, "Influence of catalytic functionalities of zeolites on product selectivities in methanol conversion" Seung-Chan Baek et al. Energy & Fuels, 2009, 23(2), pages 593-598 and "Determining an optimum catalyst for liquid-phase dehydration of methanol to dimethyl ether" Khandan, N et al. Applied Catalysis: General, vol. 349, Issues 1-2, 31 Oct. 2008, pages 6-12.

Korean patent application, KR 2009131560A describes the preparation of dimethyl ether by dehydrating methanol at 200-350° C. and 1-50 atmospheres pressure in the presence of a ferrierite based catalyst or a catalyst obtained by the partial introduction of alkali metal and/or alkaline earth metal ions.

Korean patent application, KR 20090103512 describes the preparation of dimethyl ether by dehydrating methanol in the presence of a zeolite catalyst having a defined content of an aluminium phosphate binder.

Catalysts are known for the dehydration/hydrolysis conversion of methanol and methyl acetate. U.S. Pat. No. 6,521,783 describes a process in which acetic acid, methyl acetate, methanol, dimethyl ether and water is fed to a hydrolysis/dehydration reactor which contains an ester hydrolysis catalyst and an alcohol dehydration catalyst which can be the same or different. The alcohol dehydration catalyst can be selected from a solid acid, heteropolyacids, acidic zeolites, titania or silica promoted alumina, aluminium phosphate or tungsten oxide supported on silica-alumina. The ester hydrolysis catalyst can be selected from acidic ion-exchange resins, acidic gamma alumina, fluorinated alumina, sulphate or tungstate promoted zirconia, titania or silica promoted alumina, aluminium phosphate, tungsten oxide supported on silica-alumina, clays, supported mineral acids, zeolites or heteropolyacids. In an example relating to this process the nature of the catalyst is not identified.

WO 2011027105 describes the conversion of methanol and methyl acetate to acetic acid and dimethyl ether products at temperatures of 140 to 250° C. in the presence of a zeolite catalyst which has a 2-dimensional channel system comprising at least one channel having a 10-membered ring. The zeolites identified as being of this type include ferrierite, ZSM-35 and clinoptilolite.

It has now been found that in the co-production of acetic and dimethyl ether by the dehydration and hydrolysis of methanol and methyl acetate in the presence of zeolite catalysts, zeolite catalysts such as ferrierite, with the passage of time, exhibit a loss of catalytic activity which results in a loss of productivity to the products, acetic acid and dimethyl ether. Such deactivation of the catalyst necessitates costly and time consuming regeneration processes to restore activity to the catalyst.

Typically, the dehydration and hydrolysis reaction is performed at temperatures of at least 140° C. to about 250° C. Generally, it is beneficial to perform the reaction at higher temperatures in order to achieve more attractive production rates. However, it has also been observed that zeolite catalysts useful for the reaction deactivate much more rapidly at higher reaction temperatures.

Furthermore, depending on their source, the methanol and/or methyl acetate feedstock may contain certain impurities such as acetone. It has now been found that the presence of such impurities, particularly at relatively high levels thereof, are deleterious to the zeolite catalysts. Unless steps are taken to remove such impurities from the methanol and/or methyl acetate feedstocks prior to contact with the zeolite catalyst, their presence will enhance the rate at which the catalyst deactivates.

It would therefore be highly desirable to reduce the deactivation rate of zeolite catalysts for use in the co-production of acetic acid and dimethyl ether from methanol and methyl acetate feedstocks and, in particular to reduce the deactivation rate of such zeolite catalysts at high reaction temperatures and/or in the presence of impurities such as acetone.

It has now been found that these above-summarized deleterious effects can be unexpectedly ameliorated by carrying out the dehydration and hydrolysis reaction using zeolites which possess a 2-dimensional channel system comprising at least one channel with a 10-membered ring and a high silica:alumina molar ratio. In particular, it has been found that such zeolites exhibit increased resistance to deactivation at high reaction temperatures and/or in the presence of acetone. Advantageously, the result of employing zeolites having the afore-mentioned characteristics is an increase in the effective life of the zeolite catalyst in processes for the dehydration and hydrolysis of methanol and methyl acetate, and, in particular, in those processes in which the feedstocks comprise acetone.

Accordingly, the present invention provides a process for the co-production of acetic acid and dimethyl ether from a mixture of methanol and methyl acetate which process comprises contacting in a reaction zone methanol feedstock and methyl acetate feedstock with a catalyst composition at a temperature from 200 to 260° C. to produce acetic acid and dimethyl ether, and wherein said catalyst composition comprises a zeolite which has a 2-dimensional channel system comprising at least one channel having a 10-membered ring and a silica:alumina molar ratio of at least 22:1.

The present invention further provides a catalyst composition having improved lifetime in a process for the co-production of acetic acid and dimethyl ether from a mixture of methanol and methyl acetate conducted at a temperature from 200 to 260° C. wherein said catalyst composition comprises a zeolite which has a 2-dimensional channel system comprising at least one channel having a 10-membered ring and a silica:alumina molar ratio of at least 22:1.

Within the scope of the present description, the term "zeolite" is to be understood as a zeolite having a 2-dimensional channel system comprising at least one channel having a 10-membered ring.

Zeolites occur naturally and may also be prepared synthetically. Zeolites are crystalline materials of the aluminosilicate type with a three-dimensional structure of tetrahedra of aluminium and silicon which are co-ordinated tetrahedrally with oxygen atoms. These tetrahedral are joined together by means of oxygen atoms that they have in common. The channel systems formed by the crystalline network enable zeolites to be used as catalysts and are described as being 0-, 1-, 2- or 3-dimensional. The zeolites found to be useful in the present invention possess a 2-dimensional channel system. The International Zeolite Association employs a three-letter code nomenclature to classify zeolites according to their framework structure type. Information about zeolites, their framework structure types and channel systems is published in the Atlas of Zeolite Framework Types, C. H. Baerlocher, L. B. Mccusker and D. H. Olson, 6th Revised Edition, Elsevier, Amsterdam, 2007 and is also available on the website of the International Zeolite Association at www.iza-online.org.

In the present invention, the 2-dimensional channel system of the zeolite comprises at least one channel having a 10-membered ring and may comprise one or more additional channels which have rings containing 4, 5, 6, 8, 10, 12, 14 or 16 members.

Preferably, the zeolite for use in the present invention has a 2-dimensional channel system having at least one channel which has a 10-membered ring and also at least one channel which has an 8-membered ring. Examples of such zeolites include zeolites of framework structures FER (for example ferrierite, ZSM-35, ISI-6 and FU-9), HEU (for example clinoptilolite), MFS (for example ZSM-57), DAC (for example dachiardite) and STI (for example stilbite).

Other zeolites suitable for use in the present invention include zeolites having a framework structure selected from NES (for example NU-87), MWW (for example MCM-22) and TER (terranovaite).

Preferably, the zeolite has a framework structure selected from FER, HEU and MFS, and more preferably has the framework structure FER.

Suitably, zeolites for use in the present invention are ferrierite, ZSM-35, ZSM-57 and clinoptilite. Preferably, the zeolite is selected from ferrierite and ZSM-35 and most preferably, the zeolite is ferrierite.

The 2-dimensional channel system of the zeolite may comprise interconnecting channels or non-interconnecting channels, preferably interconnecting channels.

Zeolites are commercially available from a number of suppliers, for example from Zeolyst International Inc. and Zeochem AG, or they may be synthetically prepared. Commercially available forms or forms which may be synthetically prepared include the hydrogen form or a hydrogen precursor form, such as an alkali metal or ammonium form.

Preferably, zeolites utilised in the present invention are in their hydrogen or ammonium forms, most preferably, in the hydrogen form.

Hydrogen precursor forms of zeolites (ammonium or alkali metal forms) may readily be converted to the hydrogen form by known techniques. The alkali metal form may be converted to the ammonium form simply by contacting it with an aqueous solution containing ammonium ions which exchange with the alkali metal cations. Calcining the ammonium form will produce the hydrogen form.

Any suitable ammonium salt may be used to prepare an aqueous solution of ammonium ions. Examples of suitable ammonium salts include ammonium nitrate and ammonium chloride.

After contact of the zeolite with the aqueous solution of the ammonium salt, the zeolite may be washed with water and then dried to produce a dry zeolite having ammonium ions occupying alkali metal sites.

Subsequent to being dried, the zeolite may be calcined to convert ammonium cations to hydrogen cations.

The silica to alumina molar ratio of the zeolites utilised in the present invention is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value.

The bulk silica to alumina molar ratio (herein also termed "SAR") of natural or synthetic zeolites will vary. For example, the SAR of a zeolite, such as ferrierite, may range from as low as 10 to over 90. It has now been found that in the dehydration/hydrolysis process of the present invention, zeolites having a relatively high SAR deactivate less rapidly and therefore exhibit longer lifetimes. The SAR of a zeolite useful in the present invention is greater than 22. Suitably, a zeolite for use in the present invention has a SAR in the range 22 to 90, such as 22 to 60, 30 to 90 or 30 to 60.

Techniques for increasing the SAR of a zeolite are known. Such techniques include dealumination. Typical dealumination methods involve contacting a zeolite with steam and mineral acid in alternate steps, or contacting a zeolite with a dicarboxylic acid and steaming. These methods remove aluminium from a zeolite framework thereby increasing the SAR of the zeolite.

In a specific embodiment of the present invention, the zeolite has a framework structure FER, and is preferably ferrierite; in particular the zeolite is the hydrogen form of the FER zeolite or of ferrierite and suitably has a SAR in the range 22 to 90, such as 22 to 60, 30 to 90 or 30 to 60.

In a further embodiment, the zeolite has the framework structure FER, preferably ferrierite, more preferably ferrierite in the hydrogen form and has a SAR in the range 30 to 55.

Zeolites catalysts are commercially available or may be synthesised as fine crystalline powders. Since a powder has no significant mechanical strength, its practical applications are limited. Mechanical strength can be conferred on a zeolite by forming a zeolite aggregate, for example, a shaped body, such as a pill or extrudate. An extrudate may be formed by extruding the zeolite in the presence of a binder and drying and calcining the resulting extrudate.

Thus, suitably the catalyst composition for use in the present invention may also comprise at least one inorganic oxide binder. Examples of suitable inorganic oxide binders are silicas, aluminas, alumina-silicates, magnesium silicates, magnesium aluminium silicates, titanias, zirconias and clays, especially alumina, alumina-silicate or silica binders. Examples of suitable aluminas include boehemite type alumina and gamma alumina.

Suitably, the inorganic oxide binder may be present in the catalyst composition in an amount in the range of 10 wt % to 90 wt %, preferably, in the range of 15 wt % to 60 wt % (based on total weight of zeolite and binder).

Zeolite powders may also be formed into particles without the use of a binder. Typical catalyst particles include extrudates whose cross sections are circular or embrace a plurality of arcuate lobes extending outwardly from the central portion of the catalyst particles.

In an embodiment of the present invention, the catalyst composition comprises ferrierite, preferably in the hydrogen form, bound with an alumina binder and, suitably may be in the form of an extrudate.

In accordance with the present invention, a methanol feedstock and a methyl acetate feedstock are contacted with the zeolite catalyst composition to co-produce acetic acid and dimethyl ether. The zeolite utilised in the present invention catalyses the dehydration of methanol and the hydrolysis of methyl acetate. The methanol dehydration and methyl acetate hydrolysis reactions can be represented by equations (1) and (2) respectively:

$$2CH_3OH \rightleftharpoons CH_3OCH_3 + H_2O \quad (1)$$

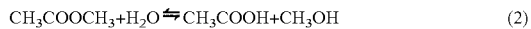

$$CH_3COOCH_3 + H_2O \rightleftharpoons CH_3COOH + CH_3OH \quad (2)$$

The methanol feedstock and the methyl acetate feedstock may be introduced into the reaction zone as a single feedstream. Preferably, however, the methanol and methyl acetate feedstocks are introduced into the reaction zone as separate feed streams.

The molar ratio of methanol and methyl acetate may be any desired ratio but suitably, the molar ratio of methanol to methyl acetate is in the range 1:0.1 to 1:40, for example 1:1 to 1:30.

The hydrolysis reaction requires water as a reactant. Water may be obtained from the dehydration reaction, which produces water in-situ. Preferably however, water is added to the process. Water may be added to the methanol and/or methyl acetate feedstocks or be introduced into the reaction zone as a separate feed. Suitably, water may be introduced into the reaction zone in an amount in the range 0.1 to 60 mol %, such as in the range 3 to 40 mol %, for example 5 to 30 mol %, based on total feed of methyl acetate, methanol and water.

Methanol and methyl acetate are produced commercially. Typically, methanol is produced on an industrial scale by the catalytic conversion of synthesis gas. Methyl acetate is produced industrially, for example, by the esterification of acetic acid with methanol. Methyl acetate may also be produced by the anhydrous carbonylation of dimethyl ether in the presence of a zeolite catalyst.

Depending on the source of the methanol and methyl acetate feedstocks to be used in the present invention, low levels of by-product components, such as one or more of acetic acid, dimethyl ether, water and acetone may be present. Acetone may be present, for example in methyl acetate derived from the anhydrous zeolite catalysed carbonylation of dimethyl ether and may also be in methanol produced by the catalytic conversion of synthesis gas. The total amount of acetone present in the methanol and methyl acetate produced by such processes will vary but may be present, for example in an amount from 0.005 to 5 mol %.

Acetone has a similar boiling point to methyl acetate and methanol and therefore it is difficult to separate acetone from these components by simple distillation techniques. However, applicant has found that acetone, even at relatively low (ppm) levels, is detrimental to the deactivation of certain zeolite catalysts, such as ferrierite, causing the catalysts to deactivate more quickly. This is particularly the case at higher reaction temperatures. It would therefore be highly desirable to provide catalysts which have reduced deactivation in processes for the conversion of methanol and methyl acetate to form dimethyl ether and acetic acid wherein at least one of the methanol and methyl acetate feedstocks comprises acetone.

Advantageously, the zeolites employed in the present invention have been found to be tolerant to acetone, even at high reaction temperatures, as shown by their reduced deactivation rates. In particular, the zeolites employed in the present invention have been found to be tolerant at acetone levels of from >0 to 5 mol % based on the total feed (including any recycles) to the reaction zone. More particularly, the zeolites employed in the present invention have been found to be tolerant at acetone levels of from >0 to 5 mol % based on the total feed (including any recycles) to the reaction zone and at high reaction temperatures.

The present invention further provides a catalyst composition having improved lifetime in a process for the co-production of acetic acid and dimethyl ether from a mixture of methanol and methyl acetate by contacting in a reaction zone methanol feedstock and methyl acetate feedstock with a catalyst composition at a temperature from 200 to 260° C. to produce acetic acid and dimethyl ether wherein said catalyst composition comprises a zeolite which has a 2-dimensional channel system comprising at least one channel having a 10-membered ring and a silica:alumina molar ratio of at least 22:1 and wherein at least one of the methanol and methyl acetate feedstocks comprises acetone.

Thus, in an embodiment of the present invention at least one of the methanol and methyl acetate feedstocks comprises acetone. Acetone may be introduced into the reaction zone in an amount of from >0 to 5 mol %, for example in an amount of from 0.5 to 5 mol %, based on total feed (including any recycles) to the reaction zone.

Suitably, the methyl acetate feedstock for use in the present invention is derived from a process for the zeolite catalysed carbonylation of dimethyl ether to produce methyl acetate and may suitably comprise acetone in an amount of from >0 to 5 mol %, such as 0.5 to 5 mol % (based on total feed, including recycles, to the reaction zone).

Alternatively and/or additionally, the methanol feedstock for use in the present invention may be derived from a process for the catalytic conversion of synthesis gas to produce methanol and may suitably comprise acetone in an amount of from >0 to 5 mol %, such as 0.5 to 5 mol % (based on total feed, including recycles, to the reaction zone).

Where acetone is present in at least one of the methyl acetate and methanol feedstocks, preferably water is introduced into the reaction zone in an amount in the range 0.1 to 60 mol %, such as in the range 3 to 40 mol %, for example in the range 5 to 30 mol %, based on the total feed to the reaction zone (including any recycles).

In a specific embodiment of the present invention, at least one of the methanol and methyl acetate feedstocks comprises acetone, for example in an amount of from >0 to 5 mol % such as in an amount of from 0.5 to 5 mol %, based on total feed (including any recycles) to the reaction zone, the zeolite catalyst employed has the framework structure FER, for example ferrierite, is suitably the hydrogen form of the FER zeolite or of ferrierite and has a SAR in the range 22 to 90, such as 30 to 90, 22 to 60 and 30 to 60.

In a further embodiment, at least one of the methanol and methyl acetate feedstocks comprises acetone, for example in an amount of from >0 to 5 mol % such as in an amount of from 0.5 to 5 mol %, based on total feed (including any recycles) to the reaction zone, the zeolite catalyst employed has the framework structure FER, for example ferrierite, is suitably the hydrogen form of the FER zeolite or of ferrierite and has a SAR in the range 22 to 90, such as 30 to 90, 22 to 60 and 30 to 60 and water is introduced into the reaction zone in an amount in the range 0.1 to 60 mol %, for example 3 to 40 mol %, such as 5 to 30 mol % based on total feed to the reaction zone (including any recycles).

In a yet further embodiment of the present invention, the zeolite is ferrierite, preferably ferrierite in its hydrogen form, and acetone is introduced into the reaction zone in an amount of from >0 to 5 mol %, such as in an amount of 0.5 to 5 mol % based on the total feed to the reaction zone (including recycles). In this embodiment, the SAR of the ferrierite may be in the range 30 to 55. Water may be introduced into the reaction zone in an amount in the range 0.1 to 60 mol %, for example 3 to 40 mol %, such as 5 to 30 mol % based on total feed to the reaction zone (including any recycles).

A diluent such as an inert gas, for example, nitrogen and helium may also be a feed to the process.

The process may be carried out in the reaction zone as a vapour phase or as a liquid phase process, for example as a fixed bed process or a slurry phase process.

Where the process is operated as a vapour phase process, the feedstocks, prior to entering the reaction zone, may be in the liquid phase. However, prior to contact with the zeolite, the liquid phase components should be volatilized, for example by use of a pre-heater.

The process is carried out at temperatures from 200 to 260° C., for example from 200 to 250° C., such as from 220 to 250° C. and 210 to 250° C.

In a specific embodiment of the present invention, the process to co-produce acetic acid and dimethyl ether is carried out by contacting methanol feedstock and methyl acetate feedstock, at least one of such feedstocks optionally comprises acetone, for example in an amount of from >0 to 5 mol %, such as 0.5 to 5 mol % based on total feed (including any recycles) to the reaction zone at a temperature in the range 220 to 250° C. or in the range 210 to 250° C. with a zeolite of framework structure FER, such as ferrierite, in particular the hydrogen form of the FER zeolite or of ferrierite and preferably having a SAR in the range 22 to 90, such as 30 to 90, 22 to 60 and 30 to 60.

In a further embodiment, the process to co-produce acetic acid and dimethyl ether is carried out by contacting methanol feedstock and methyl acetate feedstock, at least one of such feedstocks comprises acetone, for example in an amount of from >0 to 5 mol %, such as 0.5 to 5 mol % based on total feed (including any recycles) to the reaction zone at a temperature in the range 210 to 250° C. with a zeolite which is ferrierite in the hydrogen form and which ferrierite has a SAR in the range 22 to 90, such as 30 to 90, 22 to 60 or 30 to 60.

The process may be carried out at atmospheric pressure or at pressures greater than atmospheric. Where the process is carried out in the liquid phase, it is preferred to operate the process at a total reaction pressure which is sufficient to maintain the dimethyl ether product in solution. Suitably, therefore, the pressure may be at least 40 barg, such as 40 to 100 barg, suitably 40 to 60 barg. Where the process is carried out in the vapour phase, suitable operating pressures are in the range atmospheric to 30 barg, such as 2 to 20 barg.

The gas hourly space velocity (GHSV) is suitably in the range 500 to 40,000 $h^{-1}$, such as 1,000 to 25,000 $h^{-1}$, for example 1,000 to 15,000 $h^{-1}$.

The liquid hourly space velocity (LHSV) is suitably in the range 0.2 to 20, such as in the range 0.5 to 10 $h^{-1}$, for example, 0.5 to 5 $h^{-1}$ or in the range 2 to 8 $h^{-1}$.

The process may be operated as either a continuous or a batch process, preferably as a continuous process.

The product stream of the present invention comprises acetic acid and dimethyl ether. The product stream may optionally comprise water, unreacted methanol and unreacted methyl acetate. The acetic acid and dimethyl ether may be recovered from the product stream by conventional purification methods, such as by distillation. Dimethyl ether will generally be recovered as an overhead from a distillation column, and the acetic acid will typically be recovered as a bottoms fraction from the column together with any methyl acetate, methanol and water. The acetic acid can be separated from these components by further distillation. The recovered dimethyl ether may be sold or may be used as a feedstock to carbonylation processes for the production of methyl acetate. The acetic acid may be sold or may be used as a feed in other downstream processes, such as the manufacture of vinyl acetate or ethyl acetate.

The invention is now illustrated with reference to the following non-limiting Examples.

EXAMPLE 1

A series of ferrierites in the hydrogen form having SAR's of 20, 30, 40, 50, and 55 were prepared from their corresponding ammonium forms (supplied by Zeolyst International Inc.) by calcining in air for 3 hours at 500° C.

EXAMPLE 2

0.015 g of each of the ferrierite catalysts prepared in accordance with Example 1 was pressed and sieved to particles of 100 to 160 microns, loaded into a reactor and covered with 150 microliters of carborundum. Nitrogen and helium gases were flowed into the reactor at a rate of 4.4 ml/min and 0.9 ml/min respectively to provide a gas hourly space velocity of 16,000/h. The pressure was increased to 10 barg and the reactor temperature adjusted to 180° C. A vapour feed comprising 50 mol % methyl acetate, 30 mol % methanol and 20 mol % water was passed into the catalyst bed at a gas hourly space velocity of 4,000/h and held at a reactor temperature of 180° C. for 48 hours after which the temperature was increased to 220° C. for 120 hours and then reduced to 180° C. for 36 hours. The exit stream from the reactor was periodically analysed on an Interscience Trace gas chromatograph equipped with two TCD and one FID detectors and comprised acetic acid and dimethyl ether. The deactivation of a ferrierite catalyst was calculated by the loss in its activity over a period of 120 hours at 220° C. The relative deactivation rates of the catalysts are shown in Table 1. The higher the relative deactivation rate, the slower the deactivation of the catalyst.

TABLE 1

| Catalyst | SAR | Relative deactivation rate |
| --- | --- | --- |
| H-ferrierite | 20 | 1 |
| H-ferrierite | 30 | 2.6 |
| H-ferrierite | 40 | 3.2 |
| H-ferrierite | 50 | 5.3 |
| H-ferrierite | 55 | 8.4 |

As can be seen from Table 1, the use of higher SAR catalysts provides a material reduction in deactivation rate of the catalyst and hence allows for improved lifetime of the catalyst in the process.

EXAMPLE 3

Example 2 was repeated using the ferrierite catalysts prepared in accordance with Example 1 except that the composition of the feed to the reactor was 47.5 mol % methyl acetate, 28.5 mol % methanol, 19 mol % water and 5% acetone. The feed was passed into a catalyst bed at a rate of 50 microliters per minute. The reactor was maintained at 180° C. for 36 hours, then increased to 200° C. for a further 72 hours, then further increased to 220° C. for an additional 72 hours after which the temperature was reduced to 180° C. for a period of 48 hours. The exit stream from the reactor was periodically analysed on an Interscience Trace gas chromatograph equipped with two TCD detectors and one FID detector and comprised acetic acid and dimethyl ether. The deactivation of a ferrierite catalyst at temperatures of 200-220° C. was calculated by the loss in its activity over a period of 144 hours.

The relative deactivation rates of the catalysts are shown in Table 2. The higher the relative deactivation rate, the slower the deactivation of the catalyst.

TABLE 2

| Catalyst | SAR | Relative deactivation rate |
|---|---|---|
| H-ferrierite | 20 | 1 |
| H-ferrierite | 30 | 1.4 |
| H-ferrierite | 40 | 1.6 |
| H-ferrierite | 50 | 3.1 |
| H-ferrierite | 55 | 4.2 |

As can be seen from Table 2, for processes carried out in the presence of acetone, the use of higher SAR catalysts provides a significant reduction in deactivation rate of the catalyst and hence allows for improved lifetime of the catalyst in such processes.

EXAMPLE 4

The hydrolysis/dehydration process of Example 2 was repeated using H-ferrierites comprising 20 wt % alumina (ex Zeolyst International Inc.) as catalysts. The ferrierites were of SAR 20 and SAR 55. The catalysts were utilised in the form of particles formed from cylindrical extrudates having a diameter of 3.2 mm and ground and sieved to give particles of 100 to 160 microns. In this example, it was found that the deactivation of the ferrierite of SAR 55 was 6.6 times slower than that of the ferrierite of SAR 20.

EXAMPLE 5

Example 3 (hydrolysis/dehydration of methanol and methyl acetate in the presence of acetone) was repeated using H-ferrierites of SAR 20 and SAR 55 composited with 20 wt % alumina (manufacturer Zeolyst International Inc) as catalysts. The catalysts were utilised in the form of particles formed from 3.2 mm cylindrical extrudates which were ground and sieved to give particles of 100 to 160 microns. In this example, it was found that the deactivation of the ferrierite of SAR 55 was 4.4 times slower than that of the ferrierite of SAR 20.

EXAMPLE 6

H-ferrierites of SAR 20 and SAR 55 (manufacturer Zeolyst International Inc) in powder form were employed as catalysts in this example. 0.015 g of a catalyst was pressed and sieved to particles of 100-160 μm, loaded into a reactor and covered with 150 microliters of carborundum. Nitrogen and helium gases were introduced into the reactor at a rate of 4.4 mL/min and 0.9 mL/min respectively to provide a gas hourly space velocity of 16,000 $h^{-1}$. The pressure was increased to 10 barg and the reactor temperature adjusted to 180° C. A vapour feed comprising 72.0 mol % methyl acetate, 7.5 mol % methanol, 20 mol % water and 0.5 mol % acetone was passed into the catalyst bed at a gas hourly space velocity of 4,000 $h^{-1}$ and held at a reactor temperature of 180° C. for 46 hours. The temperature was then increased to 210° C. (ramp rate of 3° C./min) for 110 hours and then reduced to 180° C. for 45 hours. The temperature was then increased to 210° C. for 111 hours and then reduced to 180° C. for 55 hours. The temperature was then increased to 230° C. for 116 hours and then reduced to 180° C. for 45 hours. The temperature was then increased to 250° C. for 97 hours and then reduced to 180° C. for 35 hours. The deactivation rates (as % STY loss/day of dimethyl ether (DME) and acetic acid) of the catalysts was calculated during the second period at 210° C. and also at 230° C. and 250° C. The results are given in Table 3 below.

TABLE 3

| SAR of catalyst | DME (% STY loss/day) | | | Acetic Acid (% STY loss/day) | | |
|---|---|---|---|---|---|---|
| | 210° C. | 230° C. | 250° C. | 210° C. | 230° C. | 250° C. |
| 20 | 4.0 | 9.2 | 16.5 | 3.8 | 8.0 | 12.3 |
| 55 | 1.3 | 3.3 | 8.5 | 0.9 | 3.4 | 5.5 |

As can be seen from Table 3, for reactions carried out in the presence of acetone, the catalyst of SAR 55 deactivated at a substantially reduced rate compared to the lower SAR catalyst.

EXAMPLE 7

In this example, the hydrolysis/dehydration of a methanol and methyl acetate feedstock was carried out in the presence and absence of acetone and in the presence of a H-ferrierite catalyst composited with 20 wt % alumina (SAR 20, manufacturer Zeolyst International Inc.) and utilised in the form of particles of size 250-500 microns which were obtained by crushing and sieving 3.2 mm extrudates of the catalyst.

0.3 g of the catalyst was loaded into each of the four reactors of a 4-reactor channel micro-reactor unit. The microreactor unit comprised 4 separate Hastelloy U-shaped reactor tubes of internal diameter of 6 mm, each with their own dedicated gas (controlled using separate mass-flow control valves) and liquid feed streams. Each liquid feed stream was administered to a reactor in vapour form using a syringe drive pump. Prior to contacting a catalyst bed, the vaporised feed was mixed with 80 mol % inert gas over an inert silicon carbide pre-bed before passing it over the catalyst bed at a total gas hourly space velocity (GHSV) of about 10,500 $hr^{-1}$.

A liquid feed composition of 50 mol % methyl acetate, 30 mol % methanol and 20 mol % water was fed into reactor 1. Liquid feed compositions of methyl acetate, methanol, water with acetone added to a molar concentration of 0.5%, 1.0% and 3.0% were fed to reactors 2, 3 and 4 respectively.

Each reactor was maintained at a reaction temperature of 180° C. by means of a fluidised sand-bath heater. Each reactor had an independent pressure control and the total reaction pressure of each reactor was maintained at 10 barg. Each reaction was allowed to continue for about 450 hours. The product stream from each reactor was heated in a series of heated ovens and trace-heated lines to maintain a gas phase stream for analysis. The pressure of each product stream was let-down to atmospheric pressure prior to analysis. Each product stream was analysed periodically by gas chromatography (Agilent MicroGC) to provide composition data of the feed and product components. The effect of acetone on catalyst performance for the period 50 to 400 hours on stream is shown in Table 4 below.

TABLE 4

| Reactor | Acetone (mol %) | Rate of DME STY loss per day (g/kg/hr/day) | Rate of Acetic Acid STY loss per day (g/kg/hr/day) |
|---|---|---|---|
| 1 | no acetone | 2.7 | 4.3 |
| 2 | 0.5 | 2.8 | 5.0 |
| 3 | 1.0 | 5.0 | 6.1 |
| 4 | 3.0 | 8.3 | 9.9 |

As can clearly be seen from Table 4, the presence of acetone in the dehydration/hydrolysis reaction is harmful to the catalyst as it leads to an increase in the rate of deactivation of the catalyst.

The invention claimed is:

1. A process for the co-production of acetic acid and dimethyl ether from a mixture of methanol and methyl acetate which process comprises contacting in a reaction zone methanol feedstock and methyl acetate feedstock with a catalyst composition at a temperature from 200 to 260° C. to produce acetic acid and dimethyl ether, and wherein said catalyst composition comprises a zeolite which has a 2-dimensional channel system comprising at least one channel having a 10-membered ring and a silica:alumina molar ratio of at least 22:1.

2. A process according to claim 1 wherein the zeolite further comprises at least one channel having an 8-membered ring.

3. A process according to claim 2 wherein the zeolite has a framework structure selected from the group consisting of FER, HEU, MFS, DAC, STI, NES, MWW and TER.

4. A process according to claim 3 wherein the zeolite has the framework structure FER.

5. A process according to claim 4 wherein the zeolite of framework structure FER is ferrierite.

6. A process according to claim 1 wherein the zeolite is in the hydrogen form.

7. A process according to claim 1 wherein the zeolite has a SAR in the range 30 to 60.

8. A process according to claim 1 wherein the process is carried out at a temperature in the range 220 to 250° C.

9. A process according to claim 1 wherein at least one of the methanol and methyl acetate feedstocks comprises acetone.

10. A process according to claim 9 wherein the acetone is present in at least one of the methanol and methyl acetate feedstocks in a total amount of from >0 to 5 mol % based on the total feed (including any recycles).

11. A process according to claim 1 wherein at least one of the methanol and methyl acetate feedstocks comprises acetone, and the methanol and methyl acetate feedstocks are contacted at a temperature in the range 210 to 250° C. with a zeolite which is a ferrierite in the hydrogen form and which ferrierite has a SAR in the range 22 to 90.

12. A process according to claim 11 wherein acetone is present in at least one of the methanol and methyl acetate feedstocks in a total amount of from >0 to 5 mol % based on the total feed (including any recycles) to the reaction zone.

13. A process according to claim 1 wherein the catalyst composition comprises at least one inorganic oxide binder.

14. A process according to claim 13 wherein the binder is an alumina.

15. A process according to claim 13 wherein the catalyst composition is in the form of an extrudate.

16. A process according to claim 1 wherein the methanol and methyl acetate are in a molar ratio in the range 1:0.1 to 1:40.

17. A process according to claim 1 wherein water is introduced into the reaction zone.

18. A process according to claim 17 wherein water is introduced in an amount in the range 3 to 40 mol % based on the total feed to the reaction zone (including any recycles).

19. A process according to claim 1 wherein the process is operated in the vapour phase.

* * * * *